United States Patent [19]

Matsumura

[11] Patent Number: 4,999,009
[45] Date of Patent: Mar. 12, 1991

[54] DEVICE FOR USE WITH A CORNEA SHAPE MEASURING APPARATUS

[75] Inventor: Isao Matsumura, Yokosuka, Japan

[73] Assignee: Canon Kabushiki Kaisha, Tokyo, Japan

[21] Appl. No.: 430,974

[22] Filed: Nov. 1, 1989

Related U.S. Application Data

[63] Continuation of Ser. No. 58,579, Jun. 5, 1987, abandoned.

[30] Foreign Application Priority Data

Jun. 20, 1986 [JP] Japan .................................. 61-144431

[51] Int. Cl.$^5$ ............................................... A61B 3/10
[52] U.S. Cl. ...................................... 351/212; 351/211
[58] Field of Search ......................... 351/211, 212, 247

[56] References Cited

U.S. PATENT DOCUMENTS 4,660,946 4/1987 Nakamura et al. .................. 351/212
4,660,947 4/1987 Amoils ................................. 351/212
4,764,006 8/1988 Hamano et al. ...................... 351/211

Primary Examiner—Rodney B. Bovernick
Assistant Examiner—J. P. Ryan
Attorney, Agent, or Firm—Fitzpatrick, Cella, Harper & Scinto

[57] ABSTRACT

The corneal reflection virtual image of an index mark for cornea shape measurement is displaced by a variation in the working distance, but a light beam regulating device for extracting the corneal reflection light whose principal light ray is a light ray corresponding to the direction of displacement thereof is provided at a particular position in a cornea shape measuring optical system to thereby eliminate any measurement error based on the variation in the working distance. When a different region of the cornea is to be measured with the index mark displaced in the direction of the optic axis, a predetermined principal light ray conforming to the position of the index mark in the direction of the optic axis is caused to enter the light beam regulating device.

20 Claims, 2 Drawing Sheets

DEVICE FOR USE WITH A CORNEA SHAPE MEASURING APPARATUS

This application is a continuation of application Ser. No. 07/058,579 filed June 5, 1987, now abandoned.

BACKGROUND OF THE INVENTION

1. Field of the Invention

This invention relates to a cornea shape measuring apparatus for projecting an index mark onto the cornea of an eye to be examined and measuring the shape of the cornea by the corneal reflection image thereof.

2. Related Background Art

Heretofore, in a cornea shape measuring apparatus of this type, an index mark such as a ring-like slit has been projected onto the cornea of an eye to be examined and the reflection image thereof has been received by a two-dimensional detector or the like, and the amount of distortion or the like included in the received image has been analyzed, whereby the measured value of the shape of the cornea has been obtained.

If at this time, the spacing between the cornea and the index mark is constant, any variation in the radius of curvature of the cornea will vary the inclination of the incident light beam with respect to the cornea of the eye to be examined and thus, the size of the corneal reflection image will be varied. Accordingly, by reading the size and the amount of distortion of the corneal reflection image, the radius of curvature and the distortion of the cornea can be known.

However, a variation in the spacing between the cornea and the index mark caused by an error of the setting of the apparatus in the longitudinal direction of the optical system results in a variation in the size of the corneal reflection image and therefore, the measurement data includes the variation in the size of the corneal reflection image resulting from the difference in radius of curvature and thus, it has been difficult with the prior art apparatus to obtain an accurate measured value of the radius of curvature of the cornea of the eye to be examined.

As a method for eliminating the problem that depending on the regulation of such working distance, the size of the corneal reflection image is varied to cause a measurement error, it has been proposed to project a ring-like index mark substantially from infinity through a ring-shaped cylindrical lens as described in U.S. application Ser. No. 416,355, now abandoned, U.S. application Ser. No. 520,217, now abandoned, and U.S. application Ser. No. 543,041, now abandoned.

Generally, however, the use of a cylindrical lens leads to an increased cost. Further, where various index marks which are concentric and different in radius as described in U.S. application Ser. No. 520,217, now abandoned, are projected to measure the shapes of the central portion and marginal portion of the cornea of an eye to be examined, a discrete ring-shaped cylindrical lens becomes necessary and thus, it is impossible to make the apparatus compact in the direction perpendicular to the optic axis.

SUMMARY OF THE INVENTION

It is an object of the present invention to provide a cornea shape measuring apparatus which prevents the aforementioned measurement error from occurring even for readily moving eyes to be examined by a simple, low-cost construction.

It is also an object of the present invention to provide a cornea shape measuring apparatus which can simply measure the shapes of the central portion and marginal portion of the cornea of an eye to be examined while maintaining the compactness of the apparatus.

DESCRIPTION OF THE PREFERRED EMBODIMENTS

Figure 1A:
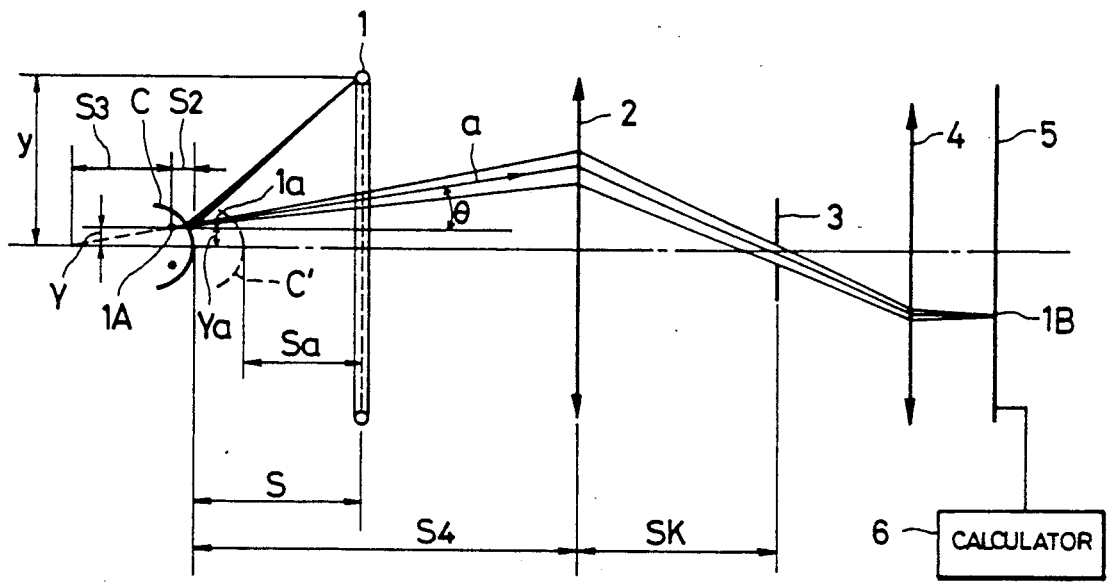
FIGS. 1A and 1B are views of a first embodiment illustrating the basic principle of the present invention.
Figure 1B:
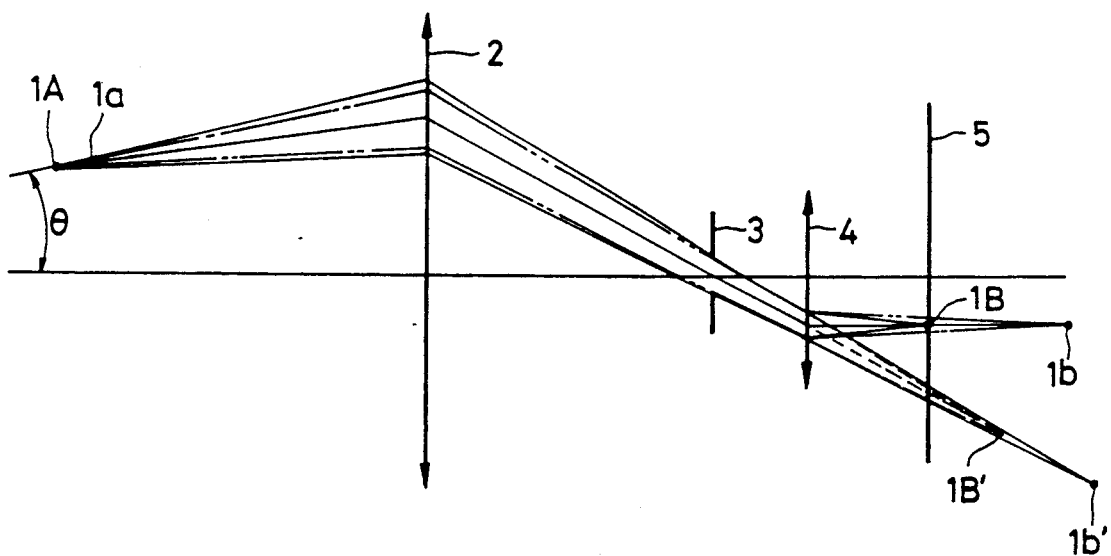
Figure 2A:
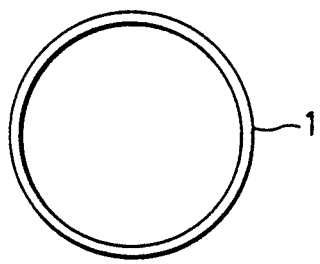
FIGS. 2A and 2B illustrate an index mark.
Figure 2B:
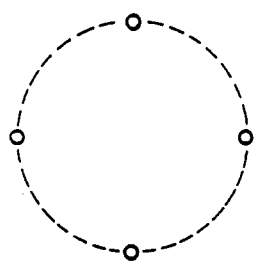

FIGS. 1A and 1B are views of a first embodiment illustrating the basic principle of the present invention. An index mark 1 is installed forwardly of the cornea C of an eye to be examined, and an objective 2, an aperture stop 3, a projection lens 4 and an imaging surface 5 such as a two-dimensional image pick-up device are successively disposed behind the index mark 1. The index mark 1 is a continuous ring light source or a substantially ring-like light source comprising a plurality of point-like light sources provided on the same circumference, as shown in FIGS. 2A and 2B, and the projection lens 4 has a forward focus at the position of the aperture stop 3 and is an image side telecentric optical system. The index mark need not be a light source itself, but may be an aperture illuminated by a light source (a so-called secondary light source).

A light beam projected from the index mark 1 onto the cornea C having a convex mirror-like surface is reflected by the cornea C while forming a ring-shaped corneal reflection image 1A called a Mire image, and forms a received light image 1B on the imaging surface 5 by the projection lens 4 through the objective 2 and the aperture stop 3, and the output signal of the imaging surface 5 is processed by a calculator 6, whereby the shape of the cornea can be measured. Depending on the convenience in the design of the apparatus, the imaging surface 5 may be disposed not at the position shown in the present embodiment, but at the conjugate position of an optical system which may be added.

The influence of the magnification of the corneal reflection image 1A upon the position of the index mark 1 will now be considered. If the radius of the ring-like index mark 1 is y and the distance between the index mark 1 and the cornea C is S and the radius of curvature of the cornea C is r and the radius of the corneal reflection image 1A is Y and the Newton's imaging equation is applied, when the distance between the index mark 1 and the cornea C is z, the following equation is established:

$$Y/y = f/z \ldots \quad (1)$$

Since the radius of curvature of the cornea C is $r$, $f = r/2$ and thus, $z = S + r/2$.

Accordingly, $Y/y = (r/2)/(S + r/2)$, and thus, $$Y = r \cdot y/(2S + r). \ldots \quad (2)$$

Assuming that when the distance S has changed to Sa, the corneal reflection image 1A becomes 1a and the radius Y thereof changes to Ya, likewise $$Ya = r \cdot y/(2Sa + r) \ldots \quad (3)$$

and the rate of the fluctuation of the corneal reflection image 1A by the fluctuation of the distance S is $$(Y - Ya)/(S - Sa) = \quad (4)$$

$$\{r \cdot y/(S - Sa)\}[\{1/(2S + r)\} - \{1/(2Sa + r)\}] =$$

$$-2r \cdot y/\{(2S + r)(2Sa + r)\}$$

because the distance from the cornea to the corneal reflection image in the direction of the optical axis can be regarded as being almost invariable.

That is, the fluctuation of the longitudinal positional relation between the cornea C and the apparatus including the index mark 1 and the objective 2 causes a magnification error along the inclination shown by equation (4). To correct this, the reflecting side light beam of the corneal reflection image 1A may be endowed with an inclination $\theta$ matching equation (4). That is, a corneal reflection light having a light ray of such inclination $\theta$ as the principal ray may be extracted.

To achieve this, the sine condition is applied with respect to the objective 2 and the direction of the emergence side principal ray is found from the direction $\theta$ of the incident principal ray a to the objective 2, thereby determining the position of the aperture stop 3. At this time, by the application of the aforementioned equation (4), the direction $\theta$ of the light ray can be found from $$\tan \theta = (Y - Ya)/(S - Sa) = -2r \cdot y/\{(2S+r)(2Sa+r)\}. \quad (5)$$

Assuming that as shown in FIG. 1A, the distance from the cornea C to the virtual image position of the image reflected by the cornea C is S2, $$1/S - 1/S2 = -2/r \ldots \quad (6)$$

and if the position S of the index mark is 80 mm and the radius of curvature r of the cornea C is 7.6 mm, then S2 = 3.99 mm is derived from equation (6).

If the radius y of the index mark 1 is 43 mm, the radius Y of the corneal reflection image 1A is found from equation (2) as follows:

$$Y = 7.6 \cdot 43/(2 \cdot 80 + 7.6) = 1.94988 \text{ mm}$$

Assuming that the distance S = 80 has increased to Sa = 80.5 mm, the size Ya of the corneal reflection image 1a is given as follows by equation (3):

$$Ya = 7.6 \cdot 43/(2 \cdot 80.5 + 7.6) = 1.93832 \text{ mm}$$

and from equation (5), $$\tan \theta = (1.94988 - 1.93832)/0.5 = 0.02312.$$

Assuming that distance on the optic axis from the position at which the principal ray a intersects the optic axis to the virtual image position is S3, S3 = 83.337 mm since $\tan \theta = Y/S3$. Also, assuming that the focal length f of the objective 2 is e.g., 50 mm and the distance S4 from the objective 2 to the cornea C is 150 mm and the distance between the objective 2 and the stop 3 is Sk, $$1/(S2 + S3 + S4) + 1/Sk = 1/f \ldots \quad (7)$$

and therefore, $1/Sk = 1/50 - 1/238.327 = 63.275$ mm and thus, if the stop 3 is disposed at the position of Sk = 63.275 mm, the size of the image provided on the imaging surface 5 will never vary even if the position of the index mark 1 somewhat fluctuates.

An attempt will now be made to varify this accuracy. According to this system, the corrected value is the difference between the amount of fluctuation and the amount of correction which results from an error of the working distance, and is mathematically expressed as—

Corrected value = $(Y - Ya) + (S - Sa) \cdot \tan \theta$.

Finding $\theta$ when S = 80 mm and Sa = 80.5 mm and r = 7.6 mm and y = 43 mm, $\tan \theta = 0.02312$, and the amount of working distance error of $\tan \theta$ and the corrected value with respect to cases where Sa = 79 mm, Sa = 79.5 mm, Sa = 80 mm, Sa = 80.5 mm and Sa = 81 mm are in the relation shown in Table 1 below

TABLE 1

| Sa | Amount of error of image height of corneal reflection image | Corrected value (amount of error of image height of corneal reflection image after corrected) |
|---|---|---|
| mm | (Y − Ya) mm | mm |
| 79 | −0.02355 | −0.00043 |
| 79.5 | −0.0117 | −0.00014 |
| 80 | 0. | 0. |
| mm | (Y − Ya) mm | mm |
| 80.5 | +0.01156 | 0. |
| 81 | +0.02299 | −0.00013 |

As is apparent from Table 1 above, the corrected value is a very small value and can be almost neglected, and when the fluctuation of (S−Sa) is less than the order of 1.0 mm, there is no possibility of the size of the obtained image being fluctuated.

Thus, only the reflection side light beam of the corneal reflection image in a direction which satisfies equation (5) enters the projection lens 4 and becomes a parallel light beam therein, and a received light image 1B which is not affected by the working distance is formed on the imaging surface 5, whereby measurement of the shape of the cornea can be accomplished.

Also, in the above-mentioned corrected value, to uniformize the corrected value about S = 80 mm which is the reference, $\tan \theta = 0.02312$ may be set as by more or less shifting it to $\tan \theta = 0.02327$.

Figure 3:
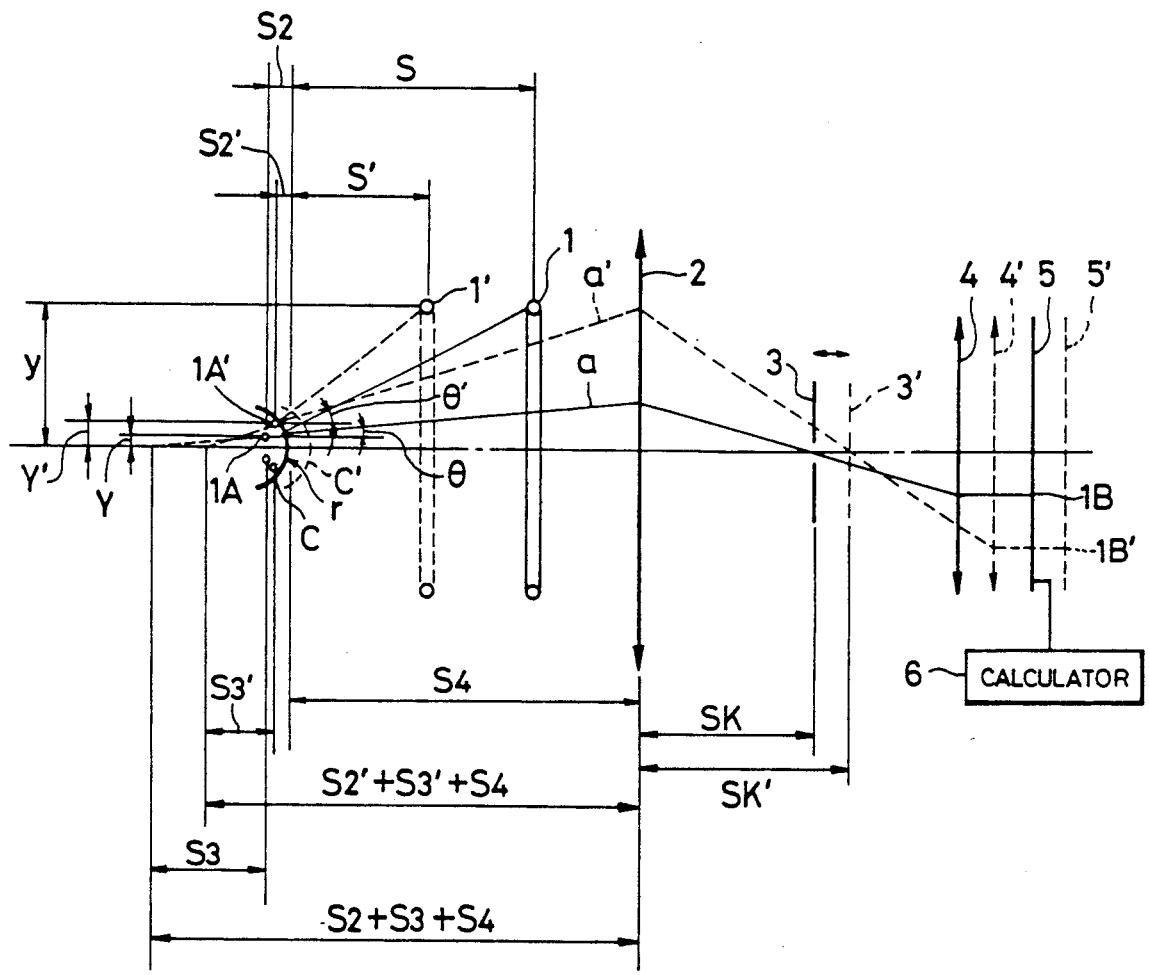
FIG. 3 shows a second embodiment which is capable of measuring the central portion and marginal portion of the cornea of an eye to be examined.

Reference is now made to FIG. 3 to describe the measurement effected at different regions on the cornea C. When measurement at different regions on the cornea C is effected with the predetermined spacing between the cornea C and the index mark being varied, the index mark 1 comes to the position of the index mark 1′, and a corneal reflection image 1A′ is formed at a position of S2′ from the cornea and the radius of the reflection image is Y′, and the rate of the fluctuation of the corneal reflection image 1A′ by the fluctuation S1 of the distance S is $$(Y' - Ya')/(S' - Sa') = \tan \theta' \ldots \quad (8)$$

Sa′ is the distance between the index mark 1′ and the cornea C′ in the direction of the optic axis, and Ya′ is the radius of the reflection image on the cornea C′. When the distance on the optic axis from the position at which the principal ray a' intersects the optic axis to the virtual image position is S3', $$S3' = Y'/\tan \theta'. \ldots \quad (9)$$

Thus, the distance Sk' between the objective 2 and the stop 3' is $$1/(S2' - S3' + S4') + 1/Sk' = 1/f \ldots \quad (10).$$

and the stop 3' moves to a new position.

Also, if with the movement of the stop 3, the projection lens 4 is moved to a position 4' by an amount equal to the amount of movement of the stop 3, a telecentric optical system will be kept. At this time, the imaging surface 5 is likewise shifted to a position 5' and the received light image fluctuates as shown by 1B'.

Figure 4:
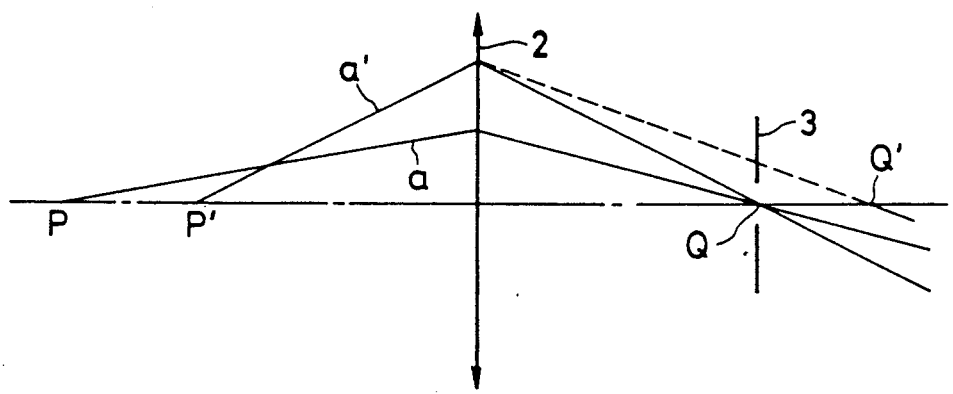
FIG. 4 shows a third embodiment.

FIG. 4 shows a construction according to another embodiment for varying the directionality characteristic of the light beam. In the previous embodiment, the position of the stop 3 is moved in conformity with the two principal rays a and a', that is, the stop 3 is disposed at the position of point Q with respect to the principal ray a and at the position of point Q' with respect to the principal ray a', whereas in the present embodiment, the points of intersection of the principal rays a and a' with the optic axis are P and P', and spherical aberration is left in the objective 2 and movement of the stop 3 is unnecessary. This is because the two principal rays a and a' both pass through the point Q.

I claim:

1. A device for use with a cornea shape measuring apparatus, comprising:
   an index mark projection means for projecting an index mark, said index mark projection means being adapted to be positioned opposite to an eye to be examined;
   an imaging optical system means for imaging a corneal reflection real image of the index mark, said imaging optical system means having an objective optical system means and an aperture; and
   image detection means for detecting the real image of the index mark, said image detection means being provided at an imaging plane of said imaging optical system means,
   wherein said aperture is locatable at a position where a ray, in a direction connecting a position of a corneal reflection virtual image when the index mark is in a correct working position spaced from the cornea to a position of a corneal reflection virtual image when the index mark is in a second position spaced from the correct working position, intersects the optical axis of said objective optical system means after passing through said objective optical system means and wherein said index mark projection means is configured and positioned to be disposed such that the ray forms an angle with an optical axis of said objective optical system means.

2. A device according to claim 1, wherein an angle $\theta$ of the light with respect to the optic axis is substantially $\tan \theta = -2r \cdot y / \{(2S+r)(2Sa+r)\}$, where r is the radius of curvature of a cornea which is the reference, y is the height of the index mark, S is the distance between the index mark and the cornea, and Sa is the distance when the distance between the index mark and the cornea is varied.

3. A device according to claim 1, wherein said imaging optical system means is telecentric on the emergence side.

4. A device according to claim 1, wherein the index mark is a ring index mark.

5. A device according to claim 1, wherein the index mark is a plurality of point-like index marks provided on the same circumference.

6. A device according to claim 1, wherein said image detection means is a two-dimensional image sensor.

7. A device according to claim 1, wherein the index mark is movable in a direction of the optical axis and said aperture is movable in the direction of the optical axis in accordance with a movement of the index mark.

8. A device according to claim 7, wherein an angle $\theta$ of the ray with respect to the optic axis is substantially $\tan \theta = -2R \cdot y / \{(2S+r)(2Sa+r)\}$, where r is the radius of curvature of a cornea which is the reference, y is the height of the index mark, S is a first distance between the index mark and the cornea, and Sa is the distance when the distance between the index mark and the cornea is varied by a predetermined amount from the first distance, and the angle $\theta'$ of the ray with respect to the optic axis is substantially $\tan \theta' = -2r \cdot y / \{(2S+r)(2Sa'+r)\}$, where S' is a second distance between the index mark and the cornea, and Sa' is the distance when the distance between the index mark and the cornea is varied by a predetermined amount from the second distance.

9. A device according to claim 7, wherein said imaging optical system means is telecentric on the emergence side.

10. A device according to claim 7, wherein the index mark is a ring index mark.

11. A device according to claim 7, wherein the index mark is a plurality of point-like index marks provided on the same circumference.

12. A device according to claim 7, wherein said image detection means is a two-dimensional image pick-up device.

13. A device according to claim 1, wherein the index mark is movable in the direction of the optical axis, said aperture is fixed in the direction of the optical axis, said objective optical system means utilizes predetermined aberration characteristics to image the corneal reflected index mark image at a position of said aperture when the index mark is in the correct working position and to image the corneal reflected index mark image at the position of said aperture when the index mark is in the second position.

14. An optical system for use with a cornea shape measuring system, comprising:
   an index mark projection means for projecting an index mark on a cornea of an eye to be examined;
   an objective optical system means for imaging a corneal reflected image of the index mark, said objective optical system means being provided coaxial with an optical axis of the eye; and
   an aperture locatable coaxially to the optical axis of the eye for restricting light flux reflected by the cornea, said aperture being located at a position so that said aperture passes a ray defined by a direction connecting a virtual image of the index mark when the index mark is in a predetermined position from the cornea and a virtual image of the index mark when the index mark is shifted from the predetermined position after passing through said objective optical system means.

wherein said index mark projection means is configured and positioned to be disposed such that the ray forms an angle with the optical axis of the eye.

15. An optical system according to claim 14, wherein an angle $\theta$ of the ray with respect to the optical axis is substantially $\tan\theta = -2r\cdot y/\{(2S+r)(2Sa+r)\}$, where r is the radius of curvature of a cornea which is the reference, y is the height of said index mark, S is the distance between the index mark and the cornea, and Sa is the distance when the distance between the index mark and the cornea is varied.

16. An optical system according to claim 14, wherein said imaging optical system means is telecentric on the emergence side.

17. An optical system according to claim 14, wherein the index mark is a ring index mark.

18. An optical system according to claim 14, wherein the index mark is a plurality of point-like index marks provided on the same circumference.

19. A device for use with a cornea shape measuring apparatus, comprising:
an index mark projection means for projecting an index mark, said index mark projection means being adapted to be positioned opposite to an eye to be examined;
an imaging optical system means for imaging a corneal reflection real image of the index mark, said imaging optical system means having an objective optical system means and an aperture; and
image detection means for detecting the real image of the index mark, said image detection means being provided at an imaging plane of said imaging optical system means, wherein said aperture is locatable at a position where a ray, in a direction connecting a position of a corneal reflection virtual image when the index mark is in a correct working position spaced from the cornea to a position of a corneal reflection virtual image when the index mark is in a second position spaced from the correct working position, intersects the optical axis of said objective optical system means after passing through said objective optical system means and wherein said index mark projection means is adapted to be located such that said ray forms an angle with an optical axis of said objective optical system means.

20. An optical system for use with a cornea shape measuring system, comprising:
an index mark projection means for projecting an index mark on a cornea of an eye to be examined;
an objective optical system means for imaging a corneal reflected image of the index mark, said objective optical system means being provided coaxial with an optical axis of the eye; and
an aperture locatable coaxially to the optical axis of the eye for restricting light flux reflected by the cornea, said aperture being located at a position so that said aperture passes a ray defined by a direction connecting a virtual image of the index mark when the index mark is in a predetermined position from the cornea and a virtual image of the index mark when the index mark is shifted from the predetermined position after passing through said objective optical system means.
wherein said index mark projection means is adapted to be located such that said ray forms an angle with the optical axis of the eye.

* * * * *

UNITED STATES PATENT AND TRADEMARK OFFICE
CERTIFICATE OF CORRECTION

PATENT NO. : 4,999,009
DATED : March 12, 1991
INVENTOR(S) : Isao Matsumura

It is certified that error appears in the above-identified patent and that said Letters Patent is hereby corrected as shown below:

COLUMN 1:

Line 43, "that" should read --that,--;
    Line 44, "distance," should read --distance--.

COLUMN 4:

Line 6, "varify" should read --verify--;
    Line 10, "as---" should read --as--;
    Line 31, "mm (Y-Ya) mm mm" should be deleted.

COLUMN 5:

Line 9, "1/(S2' - S3' + S4') + 1/Sk' = 1/f" should read
        --1/(S2' + S3' + S4') + 1/Sk' = 1/f--.

COLUMN 6:

Line 17, "tan θ = -2R·y/{(2S+r)(2Sa+r)}," should read
        --tan θ = -2r·y/{(2S+r)(2Sa+r)},--.

Signed and Sealed this

Eighth Day of December, 1992

Attest:

DOUGLAS B. COMER

Attesting Officer      Acting Commissioner of Patents and Trademarks